United States Patent [19]

Lloyd

[11] Patent Number: 4,846,829
[45] Date of Patent: Jul. 11, 1989

[54] PROTECTIVE DEVICES AND METHODS

[75] Inventor: Ronald Lloyd, Sawbridgeworth, United Kingdom

[73] Assignee: Smith and Nephew Associated Companies Limited, United Kingdom

[21] Appl. No.: 603,118

[22] Filed: Jun. 21, 1984

Related U.S. Application Data

[63] Continuation of Ser. No. 412,510, Aug. 30, 1982, abandoned, which is a continuation of Ser. No. 181,407, Aug. 26, 1980, abandoned.

[30] Foreign Application Priority Data

Aug. 29, 1979 [GB] United Kingdom ................. 7929891

[51] Int. Cl.⁴ .............................................. A61F 13/16
[52] U.S. Cl. .................................................... 604/389
[58] Field of Search ............... 604/389, 390, 385, 387, 604/366, 370

[56] References Cited

U.S. PATENT DOCUMENTS 4,023,570  5/1977  Chinai et al. ........................ 604/387
4,136,699  1/1979  Collins et al. .

FOREIGN PATENT DOCUMENTS 2537748  3/1977  Fed. Rep. of Germany .

Primary Examiner—C. Fred Rosenbaum
Attorney, Agent, or Firm—Jacobs & Jacobs

[57] ABSTRACT

A pad for protecting female undergarments from light vaginal discharges is described in which pad a body liquid impermeable layer of pressure sensitive adhesive serves to prevent transmission of body liquids through the pad and also serves to adhere the pad to the undergarment.

8 Claims, 3 Drawing Sheets

PROTECTIVE DEVICES AND METHODS

This is a continuation of Ser. No. 412,510 filed Aug. 30, 1982 which is a continuation of Ser. No. 181,407 filed Aug. 26, 1980 both now abandoned.

This invention is concerned with improvements in and relating to devices for protecting garments from contamination with body fluids and with the methods of use of such devices.

Garments in contact with the human body may become contaminated or stained by body liquids. In particular female undergarments such as panties may be contaminated or stained by light vaginal discharges. A number of disposable devices for such undergarments have been described, for example in U.S. Pat. Nos. 3,315,677, 3,463,154, 3,570,491, 3,805,790, 3,881,490, 3,881,491, 4,023,570, 4,023,571, 4,059,114 and 4,136,699, where the devices have been referred to as pads, liners, shields and the like. In general such known disposable pads have comprised one or more layers of absorbent material backed by a liquid impermeable backing layer which is provided with a layer of pressure sensitive adhesive which in turn is provided with a removable cover layer. In use the removable protective layer is stripped off to unmask the adhesive and the device then applied to the undergarment.

An important criterion for disposable daily use pads is that they are flexible and slim. It is therefore desirable that the pads have as few different layers as conveniently possible. Additionally such pads should be easily manufactured and thus relatively inexpensive. It has now been discovered that use of an impermeable pressure sensitive adhesive layer in place of the impermeable backing plus pressure sensitive adhesive layers of known pads aids in the preparation of flexible, slim, easily manufactured pads.

Thus in one aspect this invention provides a pad for protecting female undergarments from light vaginal discharges in which pad a body liquid impermeable layer of pressure sensitive adhesive serves to prevent transmission of body liquids through the pad and also serves to adhere the pad to the undergarment.

From another aspect this invention provides a pad for protecting female undergarments from light vaginal discharges which pad comprises a layer of absorbent material, a body liquid impermeable layer of pressure sensitive adhesive thereon and a cover layer over the adhesive which cover layer may be removed to expose adhesive.

From a further aspect this invention provides a pad for protecting garments from contamination by body liquids which pad comprises a shaped absorbent member provided on one surface thereof with a layer of pressure sensitive adhesive which layer is impermeable to body liquids and is, itself provided with a cover layer removable therefrom to expose at least a part thereof.

The absorbent member used in this invention will have two major faces, namely the body contacting face and the face to which the adhesive is applied. The major faces will generally be about 12 to 18 cm long and about 4.5 k to 7.5 cm wide, more generally 14 to 16 cm long and 5 to 6 cm wide. The absorbent member may be rectangular, substantially rectangular with rounded edges or may be oval with maximum dimensions as indicated or other convenient shape.

The absorbent material used in this invention may be any convenient fabric or foam. The fabric used will advantageously be a non-woven fabric for example one made from cellulosic materials such as rayon fibres, cotton linters, wood pulp fibres or cotton staple. The foam used will normally be a plastics foam, for example of a hydrophilic polyurethane. Most suitably the absorbent materials used will be soft and pleasant to the touch so that the device of this invention may be used without the necessity for an additional cover layer over the body contact surface (although of course such a layer may be included if desired). The absorbent member (that is the absorbent layer) is most suitably fairly thin, for example 1 to 4 mm, and more usually 3 or 4 mm. The absorbent layer may be of unitary construction or, if desired, may be a composite structure. Generally a unitary construction is most suitable but when the material lacks mechanical strength it may be advantageous to reinforce it with one or more layers of stronger material such as a plastics net. Particularly suitable materials are formed from rayon. A preferred absorbent material is stitch bonded rayon (a viscose rayon). Other favoured materials include spray bonded rayon and compacted rayon.

The weight of the absorbent layer is aptly from 70 gsm to 150 gsm, most desirably from 90 gsm to 120 gsm and preferably about 100 gsm.

Since the adhesive layer serves to prevent the passage of body liquids through the pad it will be substantially free from holes which would let the liquids pass through. Since the adhesive provides the barrier layer it is most suitable that the adhesive layer extends over the whole of the operative area of the major surfaces of the pad. In a preferred form the adhesive layer extends over substantially the whole of one of the major surfaces (the panty contacting surface when in use) of the pad.

The adhesive layer used in the pad will aptly weigh from 20 gsm to 120gsm, more aptly from 40 gsm to 100 gsm, for example about 60 gsm. (For conventional sized devices of this invention this results in the use of from about 0.25 g to 0.75 g of adhesive and preferably about 0.5 g of adhesive per pad).

Suitable adhesive for use in this invention will be non-toxic, water insoluble, film forming pressure sensitive adhesives such as those based on polyacrylic acid derivatives or natural or synthetic rubbers. Apt adhesives include those known to be suitable as surgical pressure sensitive adhesives or those known to be suitable for tapes such as those in diapers and similar adhesives. Preferably the adhesive is a hot melt adhesive (i.e. capable of being directly applied in molten form).

A particularly suitable hot melt pressure sensitive adhesive is a rubber based adhesive known as Dispomelt 034-1194 from Bational Adhesives & Resins Ltd., Slough, Bucks.U.K. This has a melt viscosity of 900 centipoises at 180° C. and 2200 centipoises at 150° C. as measured on a Brookfield Thermocell. This adhesive has the desirable characteristics of being water white in colour and having a high tack combined with good cohesive strength.

If desired the layer of pressure sensitive adhesive can be provided by a double sided adhesive tape with the proviso that the flimsy tape must not itself act as a fluid barrier and must merely act as a carrier for the pressure sensitive adhesive. If such a tape is used only the garment-contacting side need carry an adhesive which is pressure sensitive. The adhesive on the absorbent layer facing side of the tape may be a pressure sensitive adhesive or, if desired may be a contact adhesive (i.e. a non-peelable adhesive). The advantage of using two types of adhesive in this manner is that the contact adhesive shows less tendency to peel free of the absorbent layer than the pressure sensitive adhesive does from the garment and so renders peeling from the garment after use yet more convenient. For this invention the definition of body liquid impermeable pressure sensitive adhesives includes composite adhesives in which the garment facing layer is pressure sensitive and the layer as a whole is liquid impermeable.

The cover layer may be any convenient release material such as siliconised paper and the like.

The invention also provides a method for protecting a garment against contamination of body fluids which comprises removing at least part of the cover layer from a pad according to the invention and adhering the absorbent member to the garment by means of the adhesive. After use or wearing of the garment, the pad may then simply be removed from the garment and disposed of.

The pads of this invention may if desired be cut from preformed tapes in a simple cutting operation.

Thus in a further aspect this invention provides a tape which comprises a layer of absorbent material, a fluid impermeable layer of pressure sensitive adhesive thereon and a cover layer on said adhesive layer.

The substances making up the layers will, of course, be as hereinbefore described with reference to the pad of this invention.

Most desirably the tape of this invention will be 4.5 cm to 7.5 cm wide and more desirable 5 to 6 cm wide.

Preferably the layer of absorbent material and cover layer are equally wide and the layer of adhesive is slightly narrower so that an adhesive free margin of for example 0.2 to 0.4 cm wide is found at the edge of the tape.

If desired the devices of this invention may have incorporated therein odour absorbing materials, for example odour absorbing carbon, silicates or the like.

The pads of this invention may be prepared by any convenient manner. As will be apparent to the skilled worker the pads can even be prepared by hand by hot spreading a continuous layer of adhesive onto the cover layer of desired dimensions and then placing the adhesive coated cover layer onto the absorbent layer of desired dimensions. Such activities can of course be machanised in conventional manner. A highly convenient manner for preparing favoured devices of this invention is described hereinafter.

In order that the invention may be well understood reference will be made to the accompanying drawings in which.

Figure 1:
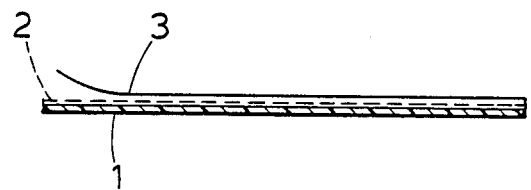
FIG. 1 is a longitudinal cross-section through a simple embodiment of pad in accordance with the invention showing the cover layer partly removed.

As shown in FIG. 1 of the drawings a protective pad in accordance with the invention comprises an absorbent member 1 having on one face thereof a layer of pressure sensitive adhesive 2 which is impermeable to body liquids and which is protected by a cover layer 3.

Figure 4:
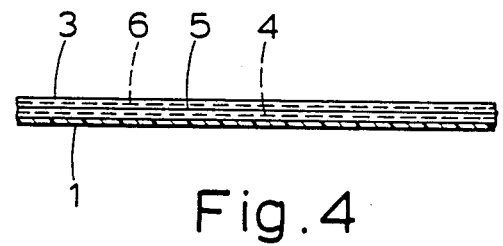
FIG. 4 is a longitudinal cross-section through another embodiment of pad in accordance with the invention.
Figure 7:
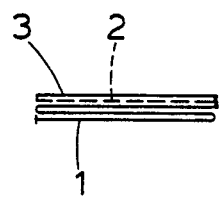
FIG. 7 is a transverse cross-section through a yet further embodiment of pad in accordance with the invention.

Absorbent member 1 is suitably fairly thin, e.g. from 1 to 4 mm in thickness, and in its simplest embodiment takes the form of a layer of a piece of absorbent material such as non-woven fabric or a plastics foam. The absorbent member may however be of composite structure and thus, for example, may take the form of non-woven fabric or plastics foam reinforced with one or more reinforcing layers, such as a layer of plastics net, either bonded to each or both faces of the non-woven fabric or foam or arranged in the body of the absorbent member. An example of such a construction is shown in FIG. 4 of the drawings in which the absorbent member takes the form of a layer 1 of absorbent material, having bonded to one face thereof, by means of adhesive layer 4, a layer of plastics net 5. Plastics nets, in turn, is provided with a further layer of body liquid impermeable adhesive 6 protected by cover 3. Alternatively member 1 may be formed of a folded layer of absorbent material, such as non-woven fabric, for example as shown in FIG. 7 of the drawings.

The layer of pressure sensitive adhesive 2 serves two purposes, namely it serves to enable the pad to be removably bonded to a garment whilst at the same time, due to its impermeable nature, serving to prevent the passage of body liquids from the pad to the garment to which it is attached.

Whilst it is necessary that adhesive layer 2 be impermeable to body liquids it is not essential that it be impermeable to moisture vapour and indeed such body liquid impermeable/moisture vapour permeable layer may be desirable in that it permits the pad to "breathe", hence rendering its use more comfortable to the wearer. Such properties may be imparted to the adhesive layer, for example, forming it as a microporous layer or as a continuous layer of a moisture vapour permeable adhesive.

Cover layer 3 serves to protect the adhesive layer 2 in transit and storage and is removed before the pad is applied to the desired garment.

Figure 2:
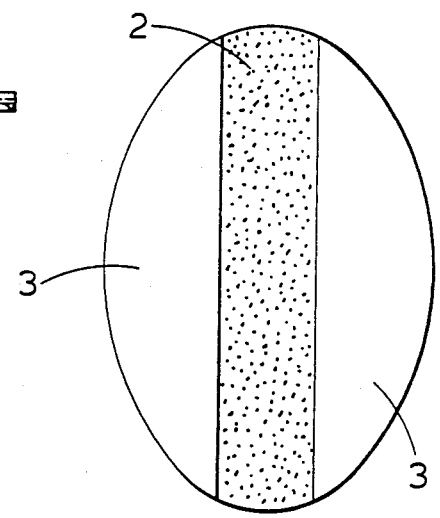
FIGS. 2 and 3 are plan views of other embodiments of pad in accordance with the invention showing only a portion of the cover layer removed.
Figure 3:
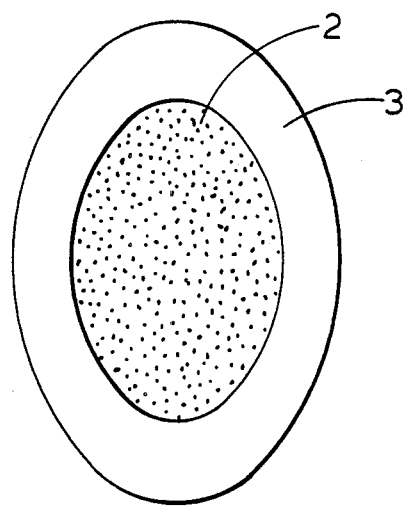

It is not necessary, in order to achieve adequate adhesion of the pad to the garment, that the whole of the cover layer be removed and indeed it may often be more desirable that the outer edges of the adhesive layer be left protected so that the chance of adhesion to the skin of the user be reduced. Thus, as shown in FIG. 2, a central strip of the cover layer may be removed to expose a corresponding strip of adhesive or, as shown in FIG. 3, an inner portion of the cover layer may be removed. In these two latter cases it is not essential that the adhesive layer be present over the whole of the surface of the absorbent member which is masked by cover layer 3. It is, however, important that any surface of layer 1 which is not masked by cover layer 3 (when the desired portion of the latter has been removed) be wholly covered by adhesive layer 2 in order to prevent the passage of body liquids onto the garment to which the pad is attached. In this connection it may however be noted that the layer of impermeable adhesive need not necessarily extend to the edges of the absorbent member, a small margin, up to a four millimetres, of uncovered absorbent material being acceptable and at the same time overcoming possible problems of adhesion to the skin of the wearer.

Figure 5:
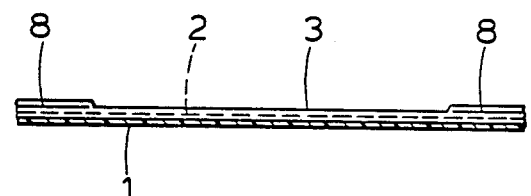
FIG. 5 is a longitudinal cross-section through a further embodiment of pad in accordance with the invention.
Figure 6:
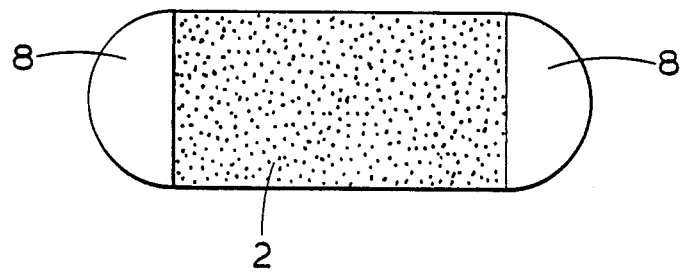
FIG. 6 is a plan view of the pad shown in FIG. 5, with the cover layer removed therefrom.

In the pad shown in FIGS. 5 and 6 of the drawings, the end surfaces of the adhesive layer 2 are protected by pieces of film 8 which are present to permanently mask the end portions of adhesive layer 2 in order to provide tabs for ready removal of the pad from a garment to which it has been adhered. Alternatively, the end portions of the absorbent member may be left uncovered with adhesive layer 2 in order to provide such tabs.

Figure 8:
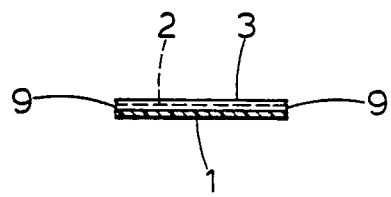

FIG. 8 is a transverse cross section through the preferred embodiment of a pad in accordance with the invention.

Figure 9:
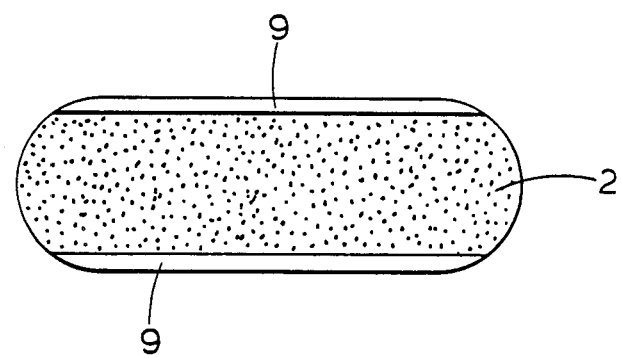

FIG. 9 is a plan view of FIG. 8 with the cover layer removed.

In the pad shown in FIGS. 8 and 9 of the drawings the liquid impermeable adhesive layer 2 does not extend to the edges of the absorbent member 1 thus providing the absorbent member 1 with two longitudinal uncoated margins 9. These margins 9 can aid the removal of cover layer 2 from the pad prior to its application to the garment and are a highly desirable feature.

Figure 10:
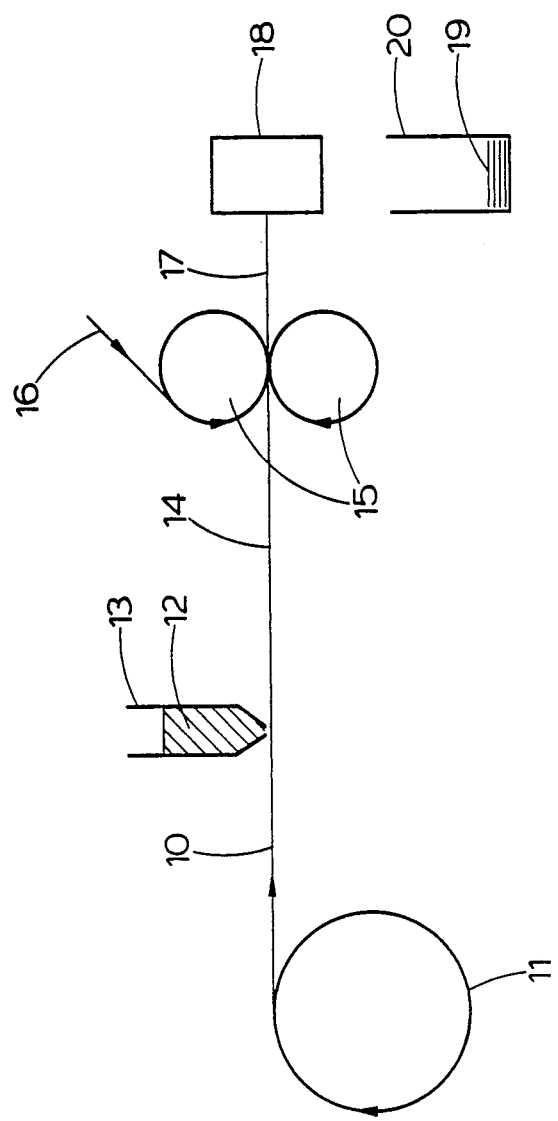

FIG. 10 illustrates a process of manufacturing the pads of this invention.

Silicone coated release paper 10 is fed from roll 11 and is coated with a hot melt pressure sensitive adhesive 12 by means of a coater 13. The adhesive coated paper 14 is fed into the nip of heated pressure rollers 15 where it is laminated to absorbent fabric 16. The laminate 17 is passed to a cutting apparatus 18 where individual panty shields 19 are cut and stacked in a receiver 20.

EXAMPLE 1

In a continuous process a 5 cm wide single sided silicone coated release paper was coated with a 4.6 cm wide central layer of hot (140° C.) pressure sensitive adhesive Dispomelt 034-1194 by means of a hot melt coater at a weight of 60 gsm. The adhesive coated release paper was laminated to a 5 cm wide 100 gsm stitch bonded rayon fabric fed from a roller onto the adhesive side of the coated paper by passage through the nip of pressure rollers heated to 80° C. The laminate was then fed into a rotary cutting apparatus which cut out individual panty shields of rectangular shape with rounded ends 15 cm long×5 cm wide.

EXAMPLE 2

A double sided silicone release paper was coated with 30 gsm of a hot melt pressure sensitive adhesive reference Bondmaster 089-2013 (Registered Trade Mark) The adhesive coated paper was laminated to 12 gsm of a polyamide spun bonded fabric Cerex (Registered Trade Mark)(from Monsanto Chemicals Ltd.) by passage through the nip of pressure rollers. The laminate was coated on the Cerex fabric surface with 20 gsm of a hot melt adhesive reference Bondmaster 089-1011 and the adhesive sheet wound up and slit into 5 cm wide rolls to a yield a double sided adhesive tape.

In a separate process the protected double sided adhesive tape was unwound and laminated to a 5 cm wide 100 gsm stitch bonded rayon fabric by passage through the nip of two pressure rollers heated to 65° C. The laminate was fed into a rotary cutting apparatus which cut out individual panty shields with rounded ends 15 cm long×5 cm wide.

What is claimed is:

1. A pad for protecting female undergarments from light vaginal discharges which pad consists essentially of (a) a layer of absorbent material 1 mm to 4 mm thick (b) a body liquid impermeable layer on one surface of said layer of absorbent material extending over substantially the whole of one major surface of the pad which impermeable layer consists essentially of a pressure sensitive adhesive and (c) a cover layer over the adhesive which cover layer may be removed to expose adhesive.

2. A pad according to claim 1 wherein the layer of absorbent material is shaped, the layer of pressure sensitive adhesive is impermeable to body liquids, and the cover layer is removable from the adhesive to expose at least a part thereof.

3. A pad according to claim 1 wherein the adhesive is a hot melt adhesive.

4. A method for protecting a garment against body fluids which comprises removing at least part of the cover layer from a pad which consists essentially of (a) a layer of absorbent material 1 mm to 4 mm thick, (b) a body liquid impermeable layer on one surface of said layer of absorbent material extending over substantially the whole of one major surface of the pad which impermeable layer consists essentially of a pressure sensitive adhesive and (c) a cover layer over the adhesive, and adhering the adhesive layer to the garment.

5. A pad for protecting female undergarments from light vaginal discharges which pad in use consists essentially of (a) a layer of absorbent material 1 mm to 4 mm thick and (b) a body liquid impermeable layer of pressure sensitive adhesive on one surface of said layer of absorbent material extending over substantially the whole of one major surface of said pad which serves to prevent transmission of body fluid through the pad and also serves to adhere the pad to the undergarment.

6. A pad according to claim 5 wherein the layer of absorbent material is shaped and the adhesive is a hot melt adhesive.

7. A method according to claim 4 wherein the layer of absorbent material is shaped, the layer of pressure sensitive adhesive is impermeable to body liquids and the cover layer is removable from the adhesive to expose at least part thereof.

8. A method according to claim 4 wherein the adhesive is a hot melt adhesive.

* * * * *